(12) United States Patent
Hirahata et al.

(10) Patent No.: US 6,242,377 B1
(45) Date of Patent: Jun. 5, 2001

(54) TRANSITION METAL COMPOUND, CATALYST COMPONENT FOR OLEFIN POLYMERIZATION, CATALYST FOR OLEFIN POLYMERIZATION, AND PROCESS FOR PRODUCING OLEFINIC POLYMER

(75) Inventors: Wataru Hirahata, Ichihara; Makoto Itagaki, Takatsuki; Kotohiro Nomura, Ikoma, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/266,626

(22) Filed: Mar. 11, 1999

(30) Foreign Application Priority Data

Mar. 13, 1998 (JP) .................................................. 10-063305

(51) Int. Cl.[7] .............................. B01J 31/00; B01J 37/00; C08F 4/02; C08F 4/60
(52) U.S. Cl. ......................... 502/117; 502/155; 502/158; 502/166; 502/167
(58) Field of Search .................................... 502/117, 155, 502/158, 166, 167

(56) References Cited

U.S. PATENT DOCUMENTS 5,866,663    2/1999  Brookhart et al. .

(List continued on next page.)

FOREIGN PATENT DOCUMENTS

| 8143623 | 6/1996 | (JP) . |
| 96/02310 | 2/1996 | (WO) . |
| 9623010 | 8/1996 | (WO) . |

OTHER PUBLICATIONS

Organometallics, 17, 3149 (1998).

(List continued on next page.)

Primary Examiner—Mark L. Bell
Assistant Examiner—J. Pasterczyk
(74) Attorney, Agent, or Firm—Stevens, Davis, Miller & Mosher, L.L.P.

(57) ABSTRACT

A transition metal compound represented by the general formula (2) or (3) described below, a catalyst component for olefin polymerization comprising said transition metal compound, a catalyst component for olefin polymerization using said transition metal compound and (C) and/or (D) described below, and a process for producing an olefinic polymer wherein olefins are homopolymerized or olefins are copolymerized with other olefins and/or other polymerizable unsaturated compound using said catalyst for olefin polymerization.

(2)

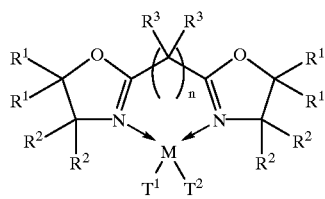

(3)

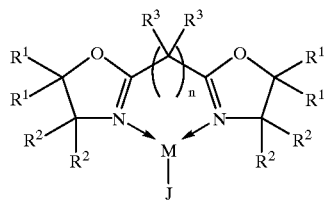

(C); A specific aluminum compound.
(D); A specific boron compound.

6 Claims, 1 Drawing Sheet

U.S. PATENT DOCUMENTS

| | | | | |
|---|---|---|---|---|
| 5,880,241 | * | 2/1999 | Brookhart et al. | 526/398 |
| 5,912,202 | * | 6/1999 | Oskam et al. | 502/117 |
| 6,034,259 | * | 3/2000 | Brookhart et al. | 502/155 |
| 6,096,676 | * | 8/2000 | Murray | 502/155 |
| 6,103,657 | * | 8/2000 | Murray | 502/155 |
| 6,103,658 | * | 8/2000 | Mackenzie et al. | 502/167 |

OTHER PUBLICATIONS

J.Am.Chem. Soc., 117, 6414 (1995).

J.Am.Chem. Soc., 118, 267 (1996).

J.Am.Chem. Soc., 118, 11664 (1996).

Journal of Molecular Catalysis, 41, 123 (1987).

Journal of Molecular Catalysis, 72, 271 (1992).

Angew.Chem.Int.Ed., 26, 1012 (1987).

J. Organometal. Chem., 544, 163 (1997).

Denmark S E et al: "Cyclopropanation with Diazomethane and Bis(Oxazoline) Palladium (II) Complexes"; Journal of Organic Chemistry, vol. 62, No. 10, May 16, 1997, pp. 3375–3389.

S. Bennett et al: "Structure and Mechanism in Aerobic Alkene Epoxidations promoted by Ruthenium Complexes of Bis(dihydrooxazole) Ligands"; Journal of the Chemical Society, Dalton Transactions, vol. 3, Jan. 1, 1995, pp. 367–376.

* cited by examiner (A) Transition metal component

M: Ni, Pd, Co, Rh, Ru
R1-3: hydrogen atom, halogen atom, alkyl group, aralkyl group, aryl group, alkoxy group, aryloxy group, aralkyloxy group, cyano group
n: $0 \leq n \leq 5$ (B) Organometal component Organoaluminum and/or Aluminoxane (C) Third component Boron compound Olefinic polymer

TRANSITION METAL COMPOUND, CATALYST COMPONENT FOR OLEFIN POLYMERIZATION, CATALYST FOR OLEFIN POLYMERIZATION, AND PROCESS FOR PRODUCING OLEFINIC POLYMER

BACKGROUND OF THE INVENTION

1. Field of the Invention

The present invention relates to a transition metal compound useful as a catalyst component for olefin polymerization, a catalyst for olefin polymerization and a process for producing an olefinic polymer. In more particular, the present invention relates to a new transition metal compound being able to be easily synthesized, a catalyst component for olefin polymerization comprising said transition metal compound, a catalyst for olefin polymerization exhibiting a high polymerization activity in polymerization of the olefin using said transition metal compound, and a process for efficiently producing an olefinic homopolymer and copolymer using said catalyst component for olefin polymerization.

2. Description of the Related Art

Reports concerning the polymerization of olefins such as ethylene, propylene and the like using a nickel and palladium compound as the transition metal component of a catalyst have been widely known. For example, a process using a complex containing a phosphorane compound as a ligand is reported in 1) U. Klabunbe, S. D. Ittel, Journal of Molecular Catalysis, Vol.41(1987), 123; U. Klabunbe, R. Mulhaupt, A. H. Janowicz, J. Calabrese and S. D. Ittel, Journal of Polymer Science, A, Polymer Chemistry, Vol.25 (1987), 1989; U. Klabunbe, T. H. Tulip, D. C. Roe and S. D. Ittel, Journal of organometallic Chemistry Vol.334(1987), 141, and 2) W. Keim, R. Appel, A. Storeck, C. Kruger and R. Goddard, Angewandte Chemie International Edition in English, Vol.26(1987), 1012, or 3) H. Nakazawa, S. Igai and K. Imaoka, Japanese Patent Publication (Unexamined) Hei 8-143623. A process using a nickel complex having a chelate type N—O ligand is reported in S. Y. Desjardins, K. J. Cavell, J. L. Hoare, B. W. Skelton, A. N. Sobolev, A. H. White and W. Keim, Journal of Organometallic Chemistry Vol.544(1997), 163, and a process using a complex having a diimine type ligand prepared by glyoxal, a diketone and acenaphthene quinone with various kind of substituted aniline compounds in 5) L. K. Johnson, C. M. Killian and M. Brookhart, Journal of American Chemical Society, Vol.117 (1995), 6414;

L. K. Johnson, S. Mecking and M. Brookhart, Journal of American Chemical Society, Vol.118(1996), 267;

C. M. Killian, D. J. Tempel, L. K. Johnson and M. Brookhart, Journal of American Chemical Society, Vol.118 (1996), 11664 and WO 96/23010.

WO 96/23010 describes in Example 205 that an oligomer is obtained by contacting ethylene with a catalyst using a complex of 2,2'-isopropylidenebis[(4s)-4-methyl-2-oxazoline]nickel bromide and methylaluminoxane.

However, these catalysts have been not always satisfied from the viewpoint of polymerization activity in olefin polymerization.

From the above-mentioned circumstances, the subject to be solved by the present invention, namely, the object of the present invention is to provide a new transition metal compound being able to be easily synthesized and useful as a catalyst component for olefin polymerization, a catalyst component for olefin polymerization comprising said transition metal compound, a catalyst for olefin polymerization exhibiting a high polymerization activity in polymerization of the olefin using said transition metal compound, and a process for efficiently producing an olefinic homopolymer and copolymer using said catalyst component for olefin polymerization.

SUMMARY OF THE INVENTION

The present invention relates to a transition metal compound represented by the following formula (2) or (3), a catalyst component for olefin polymerization comprising said transition metal compound, a catalyst for olefin polymerization using said transition metal compound and (C) and/or (D) described below, a catalyst for olefin polymerization using (A), (B), and (C) and/or (D) described below, and a process for producing an olefinic polymer wherein olefins are homopolymerized or olefins are copolymerized with other olefins and/or other polymerizable unsaturated compound using any one of catalysts for olefin polymerization.

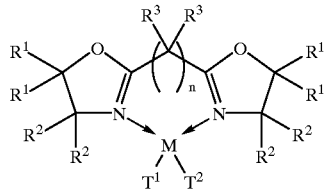

(2)

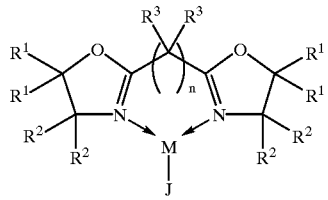

(3)

M represents a nickel atom, a palladium atom, a cobalt atom, a rhodium atom or a ruthenium atom, and J represents a coordinating compound, respectively in the general formula (2) or (3). N represents a nitrogen atom and O represents an oxygen atom. Each of $R^1$, $R^2$ and $R^3$ independently represents a hydrogen atom, a halogen atom, an alkyl group, an aryl group, an aralkyl group, an alkoxy group, an aryloxy group, an aralkyloxy group, or a cyano group, all of $R^1$s, all of $R^2$s and all of $R^3$s may be the same or different respectively, and they may be arbitrarily bonded to form a ring. Provided that all of $R^1$s are not hydrogen atoms at the same time. The symbol "n" represents an integer satisfying an equation, $0 \leq n \leq 5$. Each of $T^1$ and $T^2$ independently represents a hydrogen atom, a halogen atom, an alkyl group, an aryl group, an aralkyl group, an alkoxy group, an aryloxy group, an aralkyloxy group, a sulfonyloxy group or a substituted silyl group. $T^1$ and $T^2$ may be arbitrarily bonded to form a ring. (A); a bisoxazoline compound represented by the general formula (1) described below,

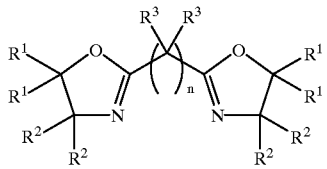

(1)

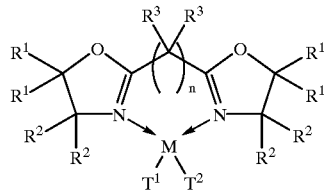

(2)

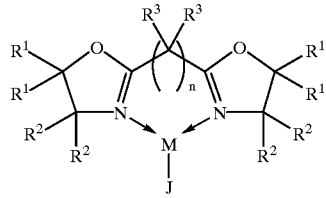

(3)

N represents a nitrogen atom and O represents an oxygen atom. Each of $R^1$, $R^2$ and $R^3$ independently represents a hydrogen atom, ahalogen atom, an alkyl group, an aryl group, an aralkyl group, an alkoxy group, an aryloxy group, an aralkyloxy group, or a cyano group, all of $R^1$s, all of $R^2$s and all of $R^3$s may be the same or different respectively, and they may be arbitrarily bonded to form a ring. Provided that all of $R^1$s are not hydrogen atoms at the same time. The symbol "n" represents an integer satisfying an equation, $0 \leq n \leq 5$.

(B); a compound of nickel, palladium, cobalt, rhodium or ruthenium.

(C) one or more of aluminum compounds selected from (C1)~(C3) described below:

(C1); an organoaluminum compound represented by the general formula, $E^1{}_a AlZ_{3-a}$, (C2); a cyclic aluminoxane having a structure represented by the general formula, $\{-Al(E^2)-O-\}_b$, (C3); a linear aluminoxane having a structure represented by the general formula, $E^3\{-Al(E^3)-O-\}_c AlE^3{}_2$, (wherein each of $E^1$, $E^2$ and $E^3$ is a hydrocarbon group, and all of $E^1$s, all of $E^2$s and all of $E^3$s may be the same or different. Z represents a hydrogen atom or a halogen atom and all of Zs may be the same or different. The symbol "a" represents a numeral satisfying an equation, $0 < a \leq 3$, b represents a numeral of 2 or more, and c represents an integer of 1 or more).

(D) a boron compound of any one of (D1)~(D3) described below:

(D1); a boron compound represented by the general formula, $BQ^1Q^2Q^3$, (D2); aboron compound represented by the general formula, $G^+(BQ^1Q^2Q^3Q^4)^-$, (D3); aboron compound represented by the general formula, $(L-H)^+(BQ^1Q^2Q^3Q^4)^-$, (wherein B is a tri-valent boron atom, $Q^1$, $Q^2$, $Q^3$ and $Q^4$ respectively are a halogen atom, an alkyl group, a halogenated alkyl group, a substituted silyl group, an alkoxy group or a di-substituted amino group and they may be the same or different. $G^+$ is an inorganic or organic cation. L is a neutral Lewis base and $(L-H)^+$ is a Brønsted acid).

DETAILED DESCRIPTION OF THE INVENTION

Figure 1:
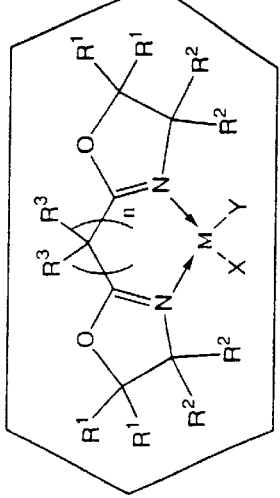
FIG. 1 is a flow-chart drawing for helping the understanding of the present invention. The present flow-chart drawing is a representative example of the mode of operation of the present invention, and the present invention is not limited to these at all.

The transition metal compound of the present invention is the transition metal compound represented by the general formula (2) or (3) described below.

In the Formulas, M represents a nickel atom, a palladium atom, a cobalt atom, a rhodium atom or a ruthenium atom, and J represents a coordinating compound, respectively in the general formula (2) or (3). N represents a nitrogen atom and O represents an oxygen atom. Each of $R^1$, $R^2$ and $R^3$ independently represents a hydrogen atom, a halogen atom, an alkyl group, an aryl group, an aralkyl group, an alkoxy group, an aryloxy group, an aralkyloxy group, or a cyano group, all of $R^1$s, all of $R^2$s and all of $R^3$s may be the same or different respectively, and they may be arbitrarily bonded to form a ring. Provided that all of $R^1$s are not hydrogen atoms at the same time. The symbol "n" represents an integer satisfying an equation, $0 \leq n \leq 5$. Each of $T^1$ and $T^2$ independently represents a hydrogen atom, a halogen atom, an alkyl group, an aryl group, an aralkyl group, an alkoxy group, an aryloxy group, an aralkyloxy group, a sulfonyloxy group or a substituted silyl group. $T^1$ and $T^2$ may be arbitrarily bonded to form a ring.

M in the above-mentioned general formula (2) or (3) represents a nickel atom, a palladium atom, a cobalt atom, a rhodium atom or a ruthenium atom, and a nickel atom or a palladium atom is preferable. In particular, a nickel atom is preferable.

J in the above-mentioned general formula (3) represents a coordinating compound and a compound capable of coordinating with the transition metal atom M. Examples of such J include olefin compounds, diene compounds, nitrile compounds, ester compounds, ether compounds and the like. More specific examples include olefin compounds such as ethylene, propylene, butene-1, pentene-1, hexene-1, heptene-1, octene-1, nonene-1, decene-1 and the like and a mixture of these isomers, cycloalkene compounds such as cyclopentene, cyclohexene, norbornene and the like, diene compounds such as butadiene, isoprene, 2,3-dimethyl-1,3-butadiene, norbornadiene, cyclopentadiene, cyclooctadiene and the like and a mixture of these isomers, nitrile compounds such as acetonitrile, benzonitrile and the like, α,β-unsaturated nitrile compounds such as acrylonitrile, propionitrile, dicyanoethylene, tetracyanoethylene and the like, ester compounds such as methylacrylate and various acrylic acid ester compounds in which methyl is changed to ethyl, n-propyl, isopropyl, isobutyl, t-butyl and the like, methylmethacrylate and various methacrylic acid ester compounds in which methyl is changed to ethyl, n-propyl, isopropyl, isobutyl, t-butyl and the like, etc., ether compounds such as tetrahydrofurane, diethyl ether, dimethoxyethane and the like, etc.

In particular, the coordinating compound having π-electron is preferable as J in the present invention, the coordinating compound having at least one olefinic double bond is more preferable, and among them, diene compounds such as 1,5-cyclooctadiene, 2,3-dimethyl-1,3-butadiene and the like are effective for stabilizing the prepared zero-valent nickel complex and the like.

Each of $R^1$, $R^2$ and $R^3$ in the above-mentioned general formula (2) or (3) independently represents a hydrogen atom, a halogen atom, an alkyl group, an aryl group, an aralkyl group, an alkoxy group, an aryloxy group, an aralkyloxy group, or a cyano group, all of $R^1$s, all of $R^2$s and all of $R^3$s may be the same or different respectively, and they may be arbitrarily bonded to form a ring. Provided that all of $R^1$s are not hydrogen atoms at the same time.

Specific examples of such halogen atom include a fluorine atom, a chlorine atom, a bromine atom, an iodine atom and the like.

An alkyl group having 1 to 20 carbon atoms is preferable as the alkyl group of $R^1$, $R^2$ or $R^3$, and examples include a methyl group, an ethyl group, a n-propyl group, an isopropyl group, a n-butyl group, an isobutyl group, a sec-butyl group, a tert-butyl group, a n-pentyl group, a neopentyl group, an amyl group, a n-hexyl group, a n-octyl group, a n-decyl group, a n-dodecyl group, a n-petnadecyl group, a n-eicosyl group and the like, and a methyl group, an ethyl group, an isopropyl group, a tert-butyl group or an amyl group is more preferable.

Any one of these alkyl groups may be substituted with a halogen atom such as a fluorine atom, a chlorine atom, a bromine atom, an iodine atom or the like. Examples of the alkyl group having 1 to 20 carbon atoms substituted with a halogen atom include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropetnadecyl group, a perfluoroeicosyl group, a perchloropropyl group, a perchlorobutyl group, a perchloropentyl group, a perchlorohexyl group, a perchlorooctyl group, a perchlorododecyl group, a perchloropetnadecyl group, a perchloroeicosyl group, a perbromopropyl group, a perbromobutyl group, a perbromopentyl group, a perbromohexyl group, a perbromooctyl group, a perbromododecyl group, a perbromopetnadecyl group, a perbromoeicosyl group and the like.

Further, any one of these alkyl groups may be partially substituted with an alkoxy group such as a methoxy group, a ethoxy group or the like, an aryloxy group such as a phenoxy group or the like, or an aralkyloxy group such as a benzyloxy group or the like.

An aryl group having 6 to 20 carbon atoms is preferable as the aryl group of $R^1$, $R^2$ or $R^3$, and examples include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, an anthrathenyl group and the like, and a phenyl group is more preferable.

Any one of these aryl groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like, or an aralkyloxy group such as a benzyloxy group or the like.

An aralkyl group having 7 to 20 carbon atoms is preferable as the aralkyl group of $R^1$, $R^2$ or $R^3$, and examples include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-dodecylphenyl)methyl group, a (n-tetradecylphenyl)methyl group, a naphthylmethyl group, an anthrathenylmethyl group and the like, and a benzyl group is more preferable.

Any one of these aralkyl groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like, or an aralkyloxy group such as a benzyloxy group or the like.

An alkoxy group having 1 to 20 carbon atoms is preferable as the alkoxy group of $R^1$, $R^2$ or $R^3$, and examples include a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group, a n-icosoxy group and the like, and a methoxy group, an ethoxy group or a tert-butoxy group is more preferable.

Any one of these alkoxy groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like, or an aralkyloxy group such as a benzyloxy group or the like.

An aryloxy group having 6 to 20 carbon atoms is preferable as the aryloxy group of $R^1$, $R^2$ or $R^3$, and examples include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group, an anthrathenoxy group and the like.

Any one of these aryloxy groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like, or an aralkyloxy group such as a benzyloxy group or the like.

An aralkyloxy group having 7 to 20 carbon atoms is preferable as the aralkyloxy group of $R^1$, $R^2$ or $R^3$, and examples include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, an (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a (n-tetradecylphenyl)methoxy group, a naphthylmethoxy group, an anthrathenylmethoxy group and the like, and a benzyloxy group is more preferable.

Any one of these aralkyloxy groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like, or an aralkyloxy group such as a benzyloxy group or the like.

An alkyl group, an aryl group or an aralkyl group is preferable as $R^1$, $R^2$ or $R^3$, and in particular, an alkyl group or an aryl group is preferable as $R^1$. A methyl group or a phenyl group is more preferable as $R^1$.

The symbol "n" in the above-mentioned general formula (2) or (3) represents an integer satisfying an equation, $0 \leq n \leq 5$, n is preferably an integer satisfying an equation, $0 \leq n \leq 2$, and in particular, n is 1 preferably.

Each of $T^1$ and $T^2$ in the above-mentioned general formula (2) independently represents a hydrogen atom, a halogen atom, an alkyl group, an aryl group, an aralkyl group, an alkoxy group, an aryloxy group, an aralkyloxy group, a sulfonyloxy group or a substituted silyl group. $T^1$ and $T^2$ may be arbitrarily bonded to form a ring.

A halogen atom, an alkyl group, an aryl group, an aralkyl group, an alkoxy group, an aryloxy group or an aralkyloxy group in $T^1$ or $T^2$ is respectively the same as in the above-mentioned $R^1$, $R^2$ or $R^3$.

The sulfonyloxy group in $T^1$ or $T^2$ represents a compound represented by the general formula, $R^5SO_3$—, and a sulfonyloxy group having 1 to 24 carbon atoms is preferable. Specifically, it includes one whose $R^5$ is an alkyl group such as a methanesulfonyloxy group, an ethanesulfonyloxy group, a dodecanesulfonyloxy group or the like, one which is partially substituted with halogen such as a trifluoromethanesulfonyloxy group or the like, and one whose $R^5$ is an aryl group such as a p-toluenesulfonyloxy group or the like.

The substituted silyl group in $T^1$ or $T^2$ is a silyl group substituted with a hydrocarbon group, wherein examples of the hydrocarbon group include alkyl groups having 1 to 10 carbon atoms such as a methyl group, an ethyl group, a n-propyl group, an isopropyl group, a n-butyl group, a sec-butyl group, a tert-butyl group, an isobutyl group, a n-pentyl group, a n-hexyl group, a cyclohexyl group and the like, aryl groups such as a phenyl group and the like, etc. Examples of such substituted silyl group having 1 to 20 carbon atoms include monosubstituted silyl groups having 1 to 20 carbon atoms such as a methylsilyl group, an ethylsilyl group, a phenylsilyl group and the like, disubstituted silyl groups having 2 to 20 carbon atoms such as a dimethylsilyl group, a diethylsilyl group, a diphenylsilyl group and the like, trisubstituted silyl groups having 3 to 20 carbon atoms such as a trimethylsilyl group, a triethylsilyl group, a tri-n-propylsilyl group, a tri-isopropylsilyl group, a tri-n-butylsilyl group, a tri-sec-butylsilyl group, a tri-tert-butylsilyl group, a tri-isobutylsilyl group, a tert-butyl-dimethylsilyl group, a tri-n-pentylsilyl group, a tri-n-hexylsilyl group, a tricyclohexylsilyl group, a triphenylsilyl group and the like, and a trimethylsilyl group, a tert-butyldimethylsilyl group or a triphenylsilyl group is preferable.

The hydrocarbon group of any one of these substituted silyl groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like, or an aralkyloxy group such as a benzyloxy group or the like.

A halogen atom, an alkyl group or an aralkyl group is preferable as $T^1$ or $T^2$ in the general formula (2), and a bromine atom, a methyl group, an isobutyl group or a benzyl group is more preferable.

A transition metal compound represented by the above-mentioned general formula (2) is preferable as the transition metal compound of the present invention.

Such transition metal compound represented by the general formula (2) or (3) can be obtained by contacting (A) the bisoxazoline compound represented by the general formula (1) describedbelow, with (B) the compoundof nickel, palladium, cobalt, rhodium or ruthenium.

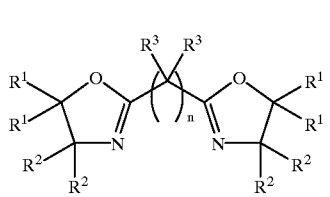

(1)

(wherein N represents a nitrogen atom and O represents an oxygen atom. Each of $R^1$, $R^2$ and $R^3$ independently represents a hydrogen atom, a halogen atom, an alkyl group, an aryl group, an aralkyl group, an alkoxy group, an aryloxy group, an aralkyloxy group, or a cyano group, all of $R^1$s, all of $R^2$s and all of $R^3$s may be the same or different respectively, and they may be arbitrarily bonded to form a ring. Provided that all of $R^1$s are not hydrogen atoms at the same time. The symbol "n" represents an integer satisfying an equation, $0 \leq n \leq 5$.)

Each of $R^1$, $R^2$, $R^3$ and n in the above-mentioned general formula (1) is the same as in the fore-mentioned general formula (2) or (3).

Asymmetric carbon atoms exist in such bisoxazoline compound (A), and at least 2 kind of optically active substances making these as asymmetric centers may exist. However, the bisoxazoline compound (A) of the present invention may be any one of the optically active substances and further a mixture thereof.

Such bisoxazoline compound (A) is a compound not described in a literature, and can be synthesized by methods below, for example, when n is 1 and substituents on two oxazoline rings are the same.

One of (optically active)2-aminoalcohols represented by the general formula (4)

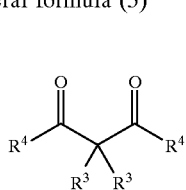

(4)

(wherein $R^1$ and $R^2$ represent the same meaning as fore-mentioned) is reacted with a malonic acid derivative represented by the general formula (5)

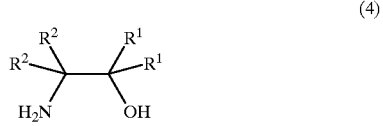

(5)

(wherein $R^3$ represents the same meaning as fore-mentioned and $R^4$ represents an alkoxy group or a halogen atom) to obtain a bisamido alcohol compound represented by the general formula (6)

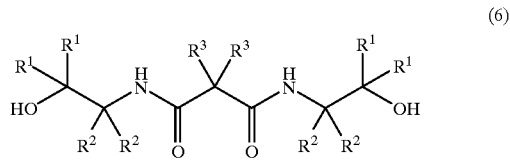

(6)

(wherein $R^1$, $R^2$ and $R^3$ represent the same meaning as fore-mentioned), and then the compound is reacted in the presence of a Lewis acid to obtain the bisoxazoline compound (A).

The bisoxazoline compound (A) except that n is 1, can be similarly obtained by suitably changing the malonic acid derivative represented by the above-mentioned general formula (5) to other compound (a 1,4-diketo compound or the like).

Wherein a salt thereof such as a hydrochloric acid salt, a sulfuric acid salt or an acetic acid salt or the like can be used as the 2-aminoalcohols (4). Among the 2-aminoalcohols (4), examples of a widely available compound or a compound capable of being easily synthesized from an amino acid ester more widely obtainable include 2-amino-1,1-dimethylpropanol, 2-amino-1,1-diethylpropanol, 2-amino-1,1-di-n-propylpropanol, 2-amino-1,1-di-isopropylpropanol, 2-amino-1,1-dicyclohexylpropanol, 2-amino-1,1-dimethoxypropanol, 2-amino-1,1-diethoxypropanol, 2-amino-1,1-diphenylpropanol, 2-amino-1,1-di-(2-methylphenyl)propanol, 2-amino-1,1-di-(3-methylphenyl)propanol, 2-amino-1,1-di-(4-methylphenyl)propanol, 2-amino-1,1-di-(2-methoxyphenyl)propanol, 2-amino-1,1-di-(3-methoxyphenyl)propanol, 2-amino-1,1-di-(4-methoxyphenyl)propanol, 1-(1-aminoethyl)cyclobutanol, 1-(1-aminoethyl)cyclopentanol, 1-(1-aminoethyl)cyclohexanol, 1-(1-aminoethyl)cycloheptanol, 2-amino-3-methyl-1,1-dimethylbutanol, 2-amino-3-methyl-1,1-diethylbutanol, 2-amino-3-methyl-1,1-di-n-propylbutanol, 2-amino-3-methyl-1,1-dicyclohexylbutanol, 2-amino-3-methyl-1,1-diphenylbutanol, 2-amino-3-methyl-1,1-di-(2-methylphenyl)butanol, 2-amino-3-methyl-1,1-di-(3-methylphenyl)butanol, 2-amino-3-methyl-1,1-di-(4-methylphenyl)butanol, 2-amino-3-methyl-1,1-di-(2-methoxyphenyl)butanol, 2-amino-3-methyl-1,1-di-(3-methoxyphenyl)butanol, 2-amino-3-methyl-1,1-di-(4-methoxyphenyl)butanol, 2-(1-amino-2-methyl-n-propyl) cyclo butanol, 1-(1-amino-2-methyl-n-propyl) cyclopen tanol, 1-(1-amino-2-methyl-n-propyl)cyclohexanol, 1-(1-amino-2-methyl-n-propyl)cycloheptanol, 2-amino-4-methyl-1,1-dimethylpentanol, 2-amino-4-methyl-1,1-diethylpentanol, 2-amino-4-methyl-1,1-di-n-propylpentanol, 2-amino-4-methyl-1,1-di-isopropylpentanol, 2-amino-4-methyl-1,1-dicyclohexylpentanol, 2-amino-4-methyl-1,1-diphenylpentanol, 2-amino-4-methyl-1,1-di-(2-methylphenyl)pentanol, 2-amino-4-methyl-1,1-di-(3-methylphenyl)pentanol, 2-amino-4-methyl-1,1-di-(4-methylphenyl)pentanol, 2-amino-4-methyl-1,1-di-(2-methoxyphenyl)pentanol, 2-amino-4-methyl-1,1-di-(3-methoxyphenyl)pentanol, 2-amino-4-methyl-1,1-di-(4-methoxyphenyl)pentanol, 1-(1-amino-3-methyl-n-butyl)cyclobutanol, 1-(1-amino-3-methyl-n-butyl)cyclopentanol, 1-(1-amino-3-methyl-n-butyl)cyclohexanol, 1-(1-amino-3-methyl-n-butyl)cycloheptanol, 2-amino-3,3-dimethyl-1,1-dimethylbutanol, 2-amino-3,3-dimethyl-1,1-diethylbutanol, 2-amino-3,3-dimethyl-1,1-di-n-propylbutanol, 2-amino-3,3-dimethyl-1,1-di-isopropylbutanol, 2-amino-3,3-dimethyl-1,1-dicyclohexylbutanol, 2-amino-3,3-dimethyl-1,1- diphenylbutanol, 2-amino-3,3-dimethyl-1,1-di-(2-methylphenyl)butanol, 2-amino-3,3-dimethyl-1,1-di-(3-methylphenyl)butanol, 2-amino-3,3-dimethyl-1,1-di-(4-methylphenyl)butanol, 2-amino-3,3-dimethyl-1,1-di-(2-methoxyphenyl)butanol, 2-amino-3,3-dimethyl-1,1-di-(3-methoxyphenyl)butanol, 2-amino-3,3-dimethyl-1,1-di-(4-methoxyphenyl)butanol, 1-(1-amino-2,2-dimethyl-n-propyl)cyclobutanol, 1-(1-amino-2,2-dimethyl-n-propyl)cyclopentanol, 1-(1-amino-2,2-dimethyl-n-propyl)cyclohexanol, 1-(1-amino-2,2-dimethyl-n-propyl)cycloheptanol, 2-amino-2-phenyl-1,1-dimethylethanol, 2-amino-2-phenyl-1,1-diethylethanol, 2-amino-2-phenyl-1,1-di-n-propylethanol, 2-amino-2-phenyl-1,1-di-isopropylethanol, 2-amino-2-phenyl-1,1-dicyclohexylethanol, 2-amino-2-phenyl-1,1-diphenylethanol, 2-amino-2-phenyl-1,1-di-(2-methylphenyl)ethanol, 2-amino-2-phenyl-1,1-di-(3-methylphenyl)ethanol, 2-amino-2-phenyl-1,1-di-(4-methylphenyl)ethanol, 2-amino-2-phenyl-1,1-di-(2-methoxyphenyl)ethanol, 2-amino-2-phenyl-1,1-di-(3-methoxyphenyl)ethanol, 2-amino-2-phenyl-1,1-di-(4-methoxyphenyl)ethanol, 1-(aminophenylmethyl)cyclobutanol, 1-(aminophenylmethyl)cyclopentanol, 1-(aminophenylmethyl)cyclohexanol, 1-(aminophenylmethyl)cycloheptanol, 2-amino-2-benzyl-1,1-dimethylethanol, 2-amino-2-benzyl-1,1-diethylethanol, 2-amino-2-benzyl-1,1-di-n-propylethanol, 2-amino-2-benzyl-1,1-di-isopropylethanol, 2-amino-2-benzyl-1,1-dicyclohexylethanol, 2-amino-2-benzyl-1,1-diphenylethanol, 2-amino-2-benzyl-1,1-di-(2-methylphenyl)ethanol, 2-amino-2-benzyl-1,1-di-(3-methylphenyl)ethanol, 2-amino-2-benzyl-1,1-di-(4-methylphenyl)ethanol, 2-amino-2-benzyl-1,1-di-(2-methoxyphenyl)ethanol, 2-amino-2-benzyl-1,1-di-(3-methoxyphenyl)ethanol, 2-amino-2-benzyl-1,1-di-(4-methoxyphenyl)ethanol, 1-(1-amino-2-phenyl)cyclobutanol, 1-(1-amino-2-phenyl)cyclopentanol, 1-(1-amino-2-phenyl)cyclohexanol, 1-(1-amino-2-phenyl)cycloheptanol and the like. The above-mentioned compound can also use a optically active substance of (R) or (S), and a mixture thereof at a certain rate can be used.

[0031]
Further, the above-mentioned 2-aminoalcohols (4) can be easily synthesized with a corresponding amino acid ester, or a salt thereof such as a hydrochloric acid salt, a sulfuric acid salt or an acetic acid salt or the like, and a corresponding Grignard reagent. Further, when an optically active aminoalcohol is synthesized, an optically active amino acid ester, or a salt thereof such as a hydrochloric acid salt, a sulfuric acid salt or an acetic acid salt or the like may be used.

Wherein the amino acid ester includes alanine methyl ester, valine methyl ester, leucine methyl ester, (t)-leucine methyl ester, phenylglycine methyl ester, phenylalanine methyl ester and compounds in which a methyl ester of these compound names is replaced with an ethyl ester, a propyl ester and a n-butyl ester.

Further, it may be a (R) or (S) compound of an optically active substituent of the above-mentioned compounds, and may be a salt such as a hydrochloric acid salt, a sulfuric acid salt, an acetic acid salt or the like of the above-mentioned esters.

The Grignard reagents include methylmagnesium chloride, ethylmagnesium chloride, isopropylmagnesium chloride, n-propylmagnesium chloride, n-butylmagnesium chloride, cyclohexylmagnesium chloride, benzylmagnesium chloride, phenylmagnesium chloride, 2-methylphenylmagnesium chloride, 3-methylphenylmagnesium chloride, 4-methylphenylmagnesium chloride, 2-methoxyphenylmagnesium chloride, 3-methoxymagnesium chloride, 4-methoxymagnesium chloride, and compounds in which chloride in the above-mentioned compound names is changed to bromide or iodide.

Examples of the malonic acid derivative represented by the general formula (5) include malonic acid diesters such as dimethyl malonate, diethyl malonate, dimethyl dimethylmalonate and the like, and malonyl dihalides such as malonyl dichloride, dimethylmalonyl dichloride, malonyl dibromide, dimethylmalonyl dibromide and the like. The amount used is usually about 0.5~2-fold mol based on the 2-amino alcohols (4), and preferably about 0.5~1-fold mol.

Examples of the Lewis acids include titanium tetra-isopropoxide, aluminum tri-isopropoxide, dimethyltin dichloride, tin chloride, zinc chloride and the like. These Lewis acids are respectively used alone or in a mixture of 2 or more thereof. The amount used is usually about 0.001~5-fold mol based on the 2-amino alcohols (4), and preferably about 0.01~1-fold mol.

A solvent is usually used at the time of reaction, and examples include a solvent such as toluene, xylene, heptane, octane, chlorobenzene, methylene chloride, ethylene dichloride or the like. These are respectively used alone or in a mixture of 2 or more thereof, and the amount used which is not specifically limited is usually about 2~200-fold weight based on the 2-amino alcohols (4).

When the fore-mentioned bisoxazoline compound (A) is produced, first of all, the bisamido alcohol compound (6) is prepared by methods below.

When the 2-amino alcohols (4) and malonic acid diesters are reacted, both are reacted using the above-mentioned solvent. The reaction temperature is usually about 50~250° C., and preferably about 60~180° C.

When the 2-amino alcohols (4) and the malonyl dichlorides are reacted, both are reacted using the above-mentioned solvent in the presence of an appropriate base. The base includes triethylamine and the like, and the amount used is usually used by about 2-fold mol or more based on malonyl dichlorides. The reaction temperature is usually about −30~100° C., and preferably about −10~50° C.

Further, the bisamido alcohol compound (6) obtained may be separated from the reaction system, and may be used for the following reaction process without separation.

As a method for producing the bisoxazoline compound (A) from the bisamido alcohol compound (6), is mentioned a method of dissolving the isolated bisamido alcohol compound (6) in the fore-mentioned solvent or adding a Lewis acid of the fore-mentioned amount to the reaction solution containing the bisamido alcohol compound, and then reacting.

The reaction temperature is usually about 50~250° C., and preferably about 60~180° C.

After completion of the reaction, the bisoxazoline compound represented by the general formula (7) which corresponds to the 2-amino alcohols (4) used can be obtained, for example, by adding an aqueous alkaline solution such as aqueous sodium hydrogencarbonate or the like to the obtained reaction mixture, separating deposited solids, concentrating the obtained filtrate, adding water to this, carrying out an extraction treatment using an organic solvent such as toluene, ethyl acetate, chloroform or the like, and concentrating the obtained organic layer. The obtained bisoxazoline compound can be further purified by a usual method such as, for example, distillation operation, chromatography treatment or the like. Further, after completion of the reaction, the desired bisoxazoline compound can be also obtained by concentrating the reaction solution and immediately carrying out an operation of distillation, chromatography or the like.

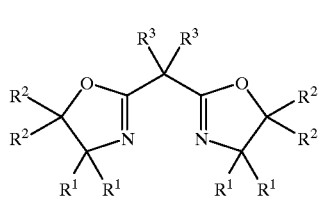

(7)

A steric configuration around an asymmetric carbon atom in the general formula (1) of the bisoxazoline compound thus obtained is similar as in a steric configuration in the optically active substituent of the 2-amino alcohols (4) used.

Among the bisoxazoline compound (A) represented by the general formula (1) of the present invention, optically active disubstituted bisoxazoline compounds obtained by the above-mentioned methods include 2,2'-methylenebis[(4R)-4-methyl-5,5-dimethyloxazoline], 2,2'-methylenebis[(4R)-4-methyl-5,5-diethyloxazoline], 2,2'-methylenebis[(4R)-4-methyl-5,5-di-n-propyloxazoline], 2,2'-methylenebis[(4R)-4-methyl-5,5-di-isopropyloxazoline], 2,2'-methylenebis[(4R)-4-methyl-5,5-dicyclohexyloxazoline], 2,2'-methylenebis[(4R)-4-methyl-5,5-dimethoxyoxazoline], 2,2'-methylenebis[(4R)-4-methyl-5,5-diethoxyoxazoline], 2,2'-methylenebis[(4R)-4-methyl-5,5-diphenyloxazoline], 2,2'-methylenebis[(4R)-4-methyl-5,5-di-(2-methylphenyl)oxazoline], 2,2'-methylenebis[(4R)-4-methyl-5,5-di-(3-methylphenyl)oxazoline], 2,2'-methylenebis[(4R)-4-methyl-5,5-di-(4-methylphenyl)oxazoline], 2,2'-methylenebis[(4R)-4-methyl-5,5-di-(2-methoxyphenyl)oxazoline], 2,2'-methylenebis[(4R)-4-methyl-5,5-di-(3-methoxyphenyl)oxazoline], 2,2'-methylenebis[(4R)-4-methyl-5,5-di-(4-methoxyphenyl)oxazoline], 2,2'-methylenebis[spiro{(4R)-4-methyloxazoline-5,1'-cyclobutane}], 2,2'-methylenebis[spiro{(4R)-4-methyloxazoline-5,1'-cyclopentane}], 2,2'-methylenebis[spiro{(4R)-4-methyloxazoline-5,1'-cyclohexane}], 2,2'-methylenebis[spiro{(4R)-4-methyloxazoline-5,1'-cycloheptane}], 2,2'-methylenebis[(4R)-4-isopropyl-5,5-dimethyloxazoline], 2,2'-methylenebis[(4R)-4-isopropyl-5,5-diethyloxazoline], 2,2'-methylenebis[(4R)-4-isopropyl-5,5-di-n-propyloxazoline], 2,2'-methylenebis[(4R)-4-isopropyl-5,5-diisopropyloxazoline], 2,2'-methylenebis[(4R)-4-isopropyl-5,5-dicyclohexyloxazoline], 2,2'-methylenebis[(4R)-4-isopropyl-5,5-diphenyloxazoline], 2,2'-methylenebis[(4R)-4-isopropyl-5,5-di-(2-methylphenyl)oxazoline], 2,2'-methylenebis[(4R)-4-isopropyl-5,5-di-(3-methylphenyl)oxazoline], 2,2'-methylenebis[(4R)-4-isopropyl-5,5-di-(4-methylphenyl)oxazoline], 2,2'-methylenebis[(4R)-4-isopropyl-5,5-di-(2-methoxyphenyl)oxazoline], 2,2'-methylenebis[(4R)-4-isopropyl-5,5-di-(3-methoxyphenyl)oxazoline], 2,2'-methylenebis[(4R)-4-isopropyl-5,5-di-(4-methoxyphenyl)oxazoline], 2,2'-methylenebis[spiro{(4R)-4-isopropyloxazoline-5,1'-cyclobutane}], 2,2'-methylenebis[spiro{(4R)-4-isopropyloxazoline-5,1'-cyclopentane}], 2,2'-methylenebis[spiro{(4R)-4-isopropyloxazoline-5,1'-cyclohexane}], 2,2'-methylenebis[spiro{(4R)-4-isopropyloxazoline-5,1'-cycloheptane}], 2,2'-methylenebis[(4R)-4-isobutyl-5,5-dimethyloxazoline], 2,2'-methylenebis[(4R)-4-isobutyl-5,5-diethyloxazoline], 2,2'-methylenebis[(4R)-4-isobutyl-5,5-di-n-propyloxazoline], 2,2'-methylenebis[(4R)-4-isobutyl-5,5-di-isopropyloxazoline], 2,2'-methylenebis[(4R)-4-isobutyl-5,5-dicyclohexyloxazoline], 2,2'-methylenebis[(4R)-4-isobutyl-5,5-diphenyloxazoline], 2,2'-methylenebis[(4R)-4-isobutyl-5,5-di-(2-methylphenyl)oxazoline], 2,2'-methylenebis[(4R)-4-isobutyl-5,5-di-(3-methylphenyl)oxazoline], 2,2'-methylenebis[(4R)-4-isobutyl-5,5-di-(4-methylphenyl)oxazoline], 2,2'-methylenebis[(4R)-4-isobutyl-5,5-di-(2-methoxyphenyl)oxazoline], 2,2'-methylenebis[(4R)-4-isobutyl-5,5-di-(3-methoxyphenyl)oxazoline], 2,2'-methylenebis[(4R)-4-isobutyl-5,5-di-(4-methoxyphenyl)oxazoline], 2,2'-methylenebis[spiro{(4R)-4-isobutyloxazoline-5,1'-cyclobutane}], 2,2'-methylenebis[spiro{(4R)-4-isobutyloxazoline-5,1'-cyclopentane}], 2,2'-methylenebis[spiro{(4R)-4-isobutyloxazoline-5,1'-cyclohexane}], 2,2'-methylenebis[spiro{(4R)-4-isobutyloxazoline-5,1'-cycloheptane}], 2,2'-methylenebis[(4R)-4-tert-butyl-5,5-dimethyloxazoline], 2,2'-methylenebis[(4R)-4-tert-butyl-5,5-diethyloxazoline], 2,2'-methylenebis[(4R)-4-tert-butyl-5,5-di-n-propyloxazoline], 2,2'-methylenebis[(4R)-4-tert-butyl-5,5-di-isopropyloxazoline], 2,2'-methylenebis[(4R)-4-tert-butyl-5,5-diphenyloxazoline], 2,2'-methylenebis[(4R)-4-tert-butyl-5,5-dicyclohexyloxazoline], 2,2'-methylenebis[(4R)-4-tert-butyl-5,5-di-(2-methylphenyl)oxazoline], 2,2'-methylenebis[(4R)-4-tert-butyl-5,5-di-(3-methylphenyl)oxazoline], 2,2'-methylenebis[(4R)-4-tert-butyl-5,5-di-(4-methylphenyl)oxazoline], 2,2'-methylenebis[(4R)-4-tert-butyl-5,5-di-(2-methoxyphenyl)oxazoline], 2,2'-methylenebis[(4R)-4-tert-butyl-5,5-di-(3-methoxyphenyl)oxazoline], 2,2'-methylenebis[(4R)-4-tert-butyl-5,5-di-(4-methoxyphenyl)oxazoline], 2,2'-methylenebis[spiro{(4R)-4-tert-butyloxazoline-5,1'-cyclobutane}], 2,2'-methylenebis[spiro{(4R)-4-tert-butyloxazoline-5,1'-cyclopentane}], 2,2'-methylenebis[spiro{(4R)-4-tert-butyloxazoline-5,1'-cyclohexane}], 2,2'-methylenebis[spiro{(4R)-4-tert-butyloxazoline-5,1'-cycloheptane}], 2,2'-methylenebis[(4R)-4-phenyl-5,5-dimethyloxazoline], 2,2'-methylenebis[(4R)-4-phenyl-5,5-diethyloxazoline], 2,2'-methylenebis[(4R)-4-phenyl-5,5-di-n-propyloxazoline], 2,2'-methylenebis[(4R)-4-phenyl-5,5-di-isopropyloxazoline], 2,2'-methylenebis[(4R)-4-phenyl-5,5-dicyclohexyloxazoline], 2,2'-methylenebis[(4R)-4-phenyl-5,5-diphenyloxazoline], 2,2'-methylenebis[(4R)-4-phenyl-5,5-di-(2-methylphenyl)oxazoline], 2,2'-methylenebis[(4R)-4-phenyl-5,5-di-(3-methylphenyl)oxazoline], 2,2'-methylenebis[(4R)-4-phenyl-5,5-di-(4-methylphenyl)oxazoline], 2,2'-methylenebis[(4R)-4-phenyl-5,5-di-(2-methoxyphenyl)oxazoline], 2,2'-methylenebis[(4R)-4-phenyl-5,5-di-(3-methoxyphenyl)oxazoline], 2,2'-methylenebis[(4R)-4-phenyl-5,5-di-(4-methoxyphenyl)oxazoline], 2,2'-methylenebis[spiro{(4R)-4-phenyloxazoline-5,1'-cyclobutane}], 2,2'-methylenebis[spiro{(4R)-4-phenyloxazoline-5,1'-cyclopentane}], 2,2'-methylenebis[spiro{(4R)-4-phenyloxazoline-5,1'-cyclohexane}], 2,2'-methylenebis[spiro{(4R)-4-phenyloxazoline-5,1'-cycloheptane}], 2,2'-methylenebis[(4R)-4-benzyl-5,5-dimethyloxazoline], 2,2'-methylenebis[(4R)-4-benzyl-5,5-diethyloxazoline], 2,2'-methylenebis[(4R)-4-benzyl-5,5-di-n-propyloxazoline], 2,2'-methylenebis[(4R)-4-benzyl-5,5-di-isopropyloxazoline], 2,2'-methylenebis[(4R)-4-benzyl-5,5-dicyclohexyloxazoline], 2,2'-methylenebis[(4R)-4-benzyl-5,5-diphenyloxazoline], 2,2'-methylenebis[(4R)-4-benzyl-5,5-di-(2-methylphenyl)oxazoline], 2,2'-methylenebis[(4R)-4-benzyl-5,5-di-(3-methylphenyl)oxazoline], 2,2'- methylenebis[(4R)-4-benzyl-5,5-di-(4-methylphenyl) oxazoline], 2,2'-methylenebis[(4R)-4-benzyl-5,5-di-(2-methoxyphenyl)oxazoline], 2,2'-methylenebis[(4R)-4-benzyl-5,5-di-(3-methoxyphenyl)oxazoline], 2,2'-methylenebis[(4R)-4-benzyl-5,5-di-(4-methoxyphenyl) oxazoline], 2,2'-methylenebis[spiro{(4R)-4-benzyloxazoline-5,1'-cyclobutane}], 2,2'-methylenebis[spiro{(4R)-4-benzyloxazoline-5,1'-cyclopentane}], 2,2'-methylenebis[spiro{(4R)-4-benzyloxazoline-5,1'-cyclohexane}], 2,2'-methylenebis[spiro{(4R)-4-benzyloxazoline-5,1'-cycloheptane}], and compounds in which (4R) in each of the above-mentioned compounds corresponds to (4S), etc.

Further, examples of the meso form isomer include a compound in which (4R) in each of the fore-mentioned compounds corresponds to (4R) of one oxazoline frame and corresponds to (4S) of the other oxazoline frame.

A compound in which a coordinating compound coordinated on an inorganic acid or organic acid salt of these transition metals or a zero-valent transition metal atom is preferable as the fore-mentioned compound (B) of nickel, palladium, cobalt, rhodium or ruthenium. Specifically, it is a chloride, a fluoride, abromide, an iodide, a carbonate, an oxalate, an acetylacetonate salt or an acetate of these transition metals, and an ether type solvent, an olefin, a diene, a nitrile compound or the like may coordinate on them at the same time. Further, in case of a zero-valent complex of nickel, palladium or the like, a compound in which an olefin, a diene, a nitrile compound or the like merely coordinated on the zero-valent complex is preferably used.

Specifically, bis(1,5-cyclooctadiene)nickel(0), bis(cyclopentadienyl)nickel(II), bis(pentamethylcyclopentadienyl)nickel(II), (hexaammine) nickel(II) chloride, (hexaammine)nickel(II) iodide, nickel (II) acetate, nickel(II) acetylacetonate, nickel(II) bromide, (dimethoxyethane)nickel(II) bromide, nickel(II) carbonate, nickel(II) chloride, (dimethoxyethane)nickel(II) chloride, nickel(II) cyclohexanebutylate, nickel(II) dimethylglyoxime, nickel(II) 2-ethylhexanoate, nickel(II) fluoride, nickel(II) hexafluoroacetylacetonate, nickel(II) iodide, nickel(II) naphthenate, nickel(II) stearate, nickel(II) trifluoroacetylacetonate, allylpalladium(II) chloride (dimer), dichlorobis(acetonitrile)palladium(II) dichlorobis(benzonitrile)palladium(II), dichloro(1,5-cyclooctadiene) palladium(II), trnas-diaminepalladium(II) dichloride, palladium(II) acetate, palladium(II) acetylacetonate, palladium(II) bromide, palladium(II) chloride, palladium(II) cyanide, palladium(II) iodide, palladium(II) trifluoroacetate, tetrakis(acetonitrile)palladium(0) tetrafluoroborate, tris (dibenzylideneacetone)dipalladium(0), cobalt(II) acetylacetonate, cobalt(III) acetylacetonate, cobalt(II) bromide, cobalt(II) carbonate, cobalt(II) chloride, cobalt(II) cyclohexanebutylate, cobalt(II) fluoride, cobalt(II) iodide, cobalt(II) naphthenate, cobalt(II) stearate, rhodium(II) bis (ethylene) acetylacetonate, bis(1,5-cyclooctadiene)rhodium (I) trifluoromethanesulfonate, chlorobis(ethylene)rhodium (I) (dimer), chloro(1,5-cyclooctadiene)rhodium(I) (dimer), chloro(norbonadiene)rhodium(I) (dimer), rhodium(II) acetate (dimer), rhodium(III) acetylacetonate, rhodium (III) chloride, rhodium(III) iodide, rhodium(II) trifluoroacetate (dimer),dichloro(1,5- cyclooctadiene)ruthenium(III) (dimer), ruthenium(III) acetylacetonate, ruthenium(III) bromide, ruthenium(III) chloride and ruthenium(III) iodide are mentioned.

Among this, a nickel compound and a palladium compound are preferable in the present invention in particular, and bis(1,5-cyclooctadiene)nickel(0), nickel(II) acetate, nickel(II) acetylacetonate, nickel(II) bromide, (dimethoxyethane)nickel(II) bromide, nickel(II) carbonate, nickel(II) chloride, (dimethoxyethane)nickel(II) chloride, nickel(II) dimethylglyoxime, nickel(II) fluoride, nickel(II) hexafluoroacetylacetonate, nickel(II) iodide, nickel(II) naphthenate, nickel(II) stearate, dichlorobis(acetonitrile) palladium(II), dichlorobis(benzonitrile)palladium(II), dichloro(1,5-cyclooctadiene)palladium(II), palladium(II) acetate, palladium(II) acetylacetonate, palladium(II) bromide, palladium(II) chloride, palladium(II) iodide andtris (dibenzylideneacetonyl)dipalladium(0) are more preferable. In particular, bis(1,5-cyclooctadiene)nickel(0), (dimethoxyethane)nickel(II) chloride and (dimethoxyethane)nickel(II) bromide are more preferably used as the transition metal compound capable of easily forming a complex with the bisoxazoline compound (A) used, in the present invention.

The transition metal compound represented by the above-mentioned general formula (2) or (3) is useful as the catalyst component for olefin polymerization. When said transition metal compound is used as the catalyst component for olefin polymerization, a cocatalyst component capable of activating said transition metal compound is used in combination.

The catalyst for olefin polymerization of the present invention is a catalyst for olefin polymerization wherein a transition metal compound represented by the above-mentioned general formula (2) or (3), and (C) and/or (D) described below are used.

(C) one or more of aluminum compounds selected from (C1)~(C3) described below:

(C1); an organoaluminum compound represented by the general formula, $E^1{}_a AlZ_{3-a}$, (C2); a cyclic aluminoxane having a structure represented by the general formula, $\{-Al(E^2)-O-\}_b$, (C3); a linear aluminoxane having a structure represented by the general formula, $E^3\{-Al(E^3)-O-\}_c AlE^3{}_2$, (wherein each of $E^1$, $E^2$ and $E^3$ is a hydrocarbon group, and all of $E^1$s, all of $E^2$s and all of $E^3$s may be the same or different. Z represents a hydrogen atom or a halogen atom and all of Zs may be the same or different. The symbol "a" represents a numeral satisfying an equation, $0<a\leq 3$, b represents a numeral of 2 or more, and c represents an integer of 1 or more.), (D) a boron compound of any one of (D1)~(D3) described below:

(D1); a boron compound represented by the general formula, $BQ^1Q^2Q^3$, (D2); a boron compound represented by the general formula, $G^+(BQ^1Q^2Q^3Q^4)^-$, (D3); aboron compound represented by the general formula, $(L-H)^+(BQ^1Q^2Q^3Q^4)^-$, (wherein B is a tri-valent boron atom, $Q^1$, $Q^2$, $Q^3$ and $Q^4$ respectively are a halogen atom, an alkyl group, a halogenated alkyl group, a substituted silyl group, an alkoxy group or a di-substituted amino group and they may be the same or different. $G^+$ is an inorganic or organic cation. L is a neutral Lewis base and $(L-H)^+$ is a Brønsted acid.).

The fore-mentioned bisoxazoline compound (A) and the fore-mentioned compound (B) may be used in place of the transition metal compound represented by the general formula (2) or (3) asthe catalyst for olefinpolymerization of the present invention. Namely, the other catalyst for olefin polymerization of the present invention is a catalyst for olefin polymerization wherein (A), (B), and (C) and/or (D) described below are used.

(A); a bisoxazoline compound represented by the general formula (1) described below, (wherein N represents a nitrogen atom and O represents an oxygen atom. Each of $R^1$, $R^2$ and $R^3$ independently represents a hydrogen atom, a halogen atom, an alkyl group, an aryl group, an aralkyl group, an alkoxy group, an aryloxy group, an aralkyloxy group, or a cyano group, all of $R^1$s, all of $R^2$s and all of $R^3$s may be the same or different respectively, and they may be arbitrarily bonded to form a ring. Provided that all of $R^1$s are not hydrogen atoms at the same time. The symbol "n" represents an integer satisfying an equation, $0 \leq n \leq 5$.), (B); a compound of nickel, palladium, cobalt, rhodium or ruthenium, (C) one or more of aluminum compounds selected from (C1)~(C3) described below:

(C1); an organoaluminum compound represented by the general formula, $E^1_a AlZ_{3-a}$, (C2); a cyclic aluminoxane having a structure represented by the general formula, $\{—Al(E^2)—O—\}_b$, (C3); a linear aluminoxane having a structure represented by the general formula, $E^3\{—Al(E^3)—O—\}_c AlE^3_2$, (wherein each of $E^1$, $E^2$ and $E^3$ is a hydrocarbon group, and all of $E^1$s, all of $E^2$s and all of $E^3$s may be the same or different. Z represents a hydrogen atom or a halogen atom and all of Zs may be the same or different. The symbol "a" represents a numeral satisfying an equation, $0 < a \leq 3$, b represents a numeral of 2 or more, and c represents an integer of 1 or more.), (D) a boron compound of any one of (D1)~(D3) described below: (D1); a boron compound represented by the general formula, $BQ^1Q^2Q^3$, (D2); a boron compound represented by the general formula, $G^+(BQ^1Q^2Q^3Q^4)^-$, (wherein B is a tri-valent boron atom, $Q^1$, $Q^2$, $Q^3$ and $Q^4$ respectively are a halogen atom, an alkyl group, a halogenated alkyl group, a substituted silyl group, an alkoxy group or a di-substituted amino group and they may be the same or different. $G^+$ is an inorganic or organic cation. L is a neutral Lewis base and $(L—H)^+$ is a Brønsted acid.).

(C) Aluminum Compound

The aluminum compound (C) used in the present invention is one or more of aluminum compounds selected from (C1)~(C3) described below:

(C1); an organoaluminum compound represented by the general formula, $E^1_a AlZ_{3-a}$, (C2); a cyclic aluminoxane having a structure represented by the general formula, $\{—Al(E^2)—O—\}_b$, (C3); a linear aluminoxane having a structure represented by the general formula, $E^3\{—Al(E^3)—O—\}_c AlE^3_2$, (wherein each of $E^1$, $E^2$ and $E^3$ is a hydrocarbon group, and all of $E^1$s, all of $E^2$s and all of $E^3$s may be the same or different. Z represents a hydrogen atom or a halogen atom and all of Zs may be the same or different. The symbol "a" represents a numeral satisfying an equation, $0 \leq a \leq 3$, b represents a numeral of 2 or more, and c represents an integer of 1 or more.)

As the hydrocarbon group in $E^1$, $E^2$ or $E^3$, a hydrocarbon group having 1 to 8 carbon atoms is preferable and an alkyl group is more preferable.

Specific examples of (C1) of the organoaluminum compound represented by the general formula, $E^1_a AlZ_{3-a}$, include trialkylaluminums such as trimethylaluminum, triethylaluminum, tripropylaluminum, triisobutylaluminum, trihexylaluminum and the like; dialkylaluminum chlorides such as dimethylaluminum chloride, diethylaluminum chloride, dipropylaluminum chloride, diisobutylaluminum chloride, dihexylaluminum chloride and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like, etc.

A trialkylaluminum is preferable, and triethylaluminum or triisobutylaluminum is more preferable.

Further, an oligomer may be prepared according to the kind of the aluminum compound used and reaction conditions (temperature and pressure) in the catalyst of the present invention.

Specific examples of $E^2$ and $E^3$ in the cyclic aluminoxane (C2) having a structure represented by the general formula, $\{—Al(E^2)—O—\}_b$, and the linear aluminoxane (C3) having a structure represented by the general formula, $E^3\{—Al(E^3)—O—\}_c AlE^3_2$, are alkyl groups such as a methyl group, an ethyl group, a n-propyl group, an isopropyl group, a n-butyl group, an isobutyl group, a n-pentyl group, a neopenyl group and the like. b is an integer of 2 or more, and c is an integer of 1 or more. $E^2$ and $E^3$ are preferably a methyl group or an isobutyl group, b is 2~40 and c is 1~40.

The above-mentioned aluminoxane is prepared by various methods. The procedure is not particularly restricted, and it may be prepared according to well-known methods. For example, it is prepared by contacting a solution of a trialkylaluminum(for example, trimethylaluminum or the like) in a suitable organic solvent (benzene, aliphatic hydrocarbon or the like) with water. Further, a method for preparing the aluminoxane by contacting a trialkylaluminum (for example, trimethylaluminum or the like) with a metal salt containing water of crystallization (for example, a hydrate of copper sulfate hydrate or the like) can be exemplified.

(D) Boron Compound

Any one of (D1); a boron compound represented by the general formula, $BQ^1Q^2Q^3$, (D2); a boron compound represented by the general formula, $G^+(BQ^1Q^2Q^3Q^4)^-$ and (D3); a boron compound represented by the general formula, $(L—H)^+(BQ^1Q^2Q^3Q^4)^-$ can be used as the boron compound (D) in the present invention.

In the boron compound (D1) represented by the general formula, $BQ^1Q^2Q^3$, B is a tri-valent boron atom, each of $Q^1$~$Q^3$ is a halogen atom, a hydrocarbon group, a halogenated hydrocarbon group, a substituted silyl group, an alkoxy group or a di-substituted amino group and they may be the same or different. Each of $Q^1$~$Q^3$ is preferably a halogen atom, a hydrocarbon group containing 1 to 20 carbon atoms, a halogenated hydrocarbon group containing 1 to 20 carbon atoms, a substituted silyl group containing 1 to 20 carbon atoms, an alkoxy group containing 1 to 20 carbon atoms or a di-substituted amino group containing 1 to 20 carbon atoms, and each of more preferable $Q^1$~$Q^3$ is a halogen atom, a hydrocarbon group containing 1 to 20 carbon atoms and a halogenated hydrocarbon group containing 1 to 20 carbon atoms. Each of $Q^1$~$Q^4$ is more preferably a fluorinated hydrocarbon group with 1 to 20 carbon atoms containing at least one fluorine atom, and in particular, each of $Q^1$~$Q^4$ is preferably a fluorinated aryl group with 6 to 20 carbon atoms containing at least one fluorine atom.

Specific examples of the compound (D1) include tris(pentafluorophenyl)borane, tris(2,3,5,6-tetrafluorophenyl)borane, tris(2,3,4,5-tetrafluorophenyl)borane, tris (3,4,5-trifluorophenyl)borane, tris(2,3,4-trifluorophenyl)borane, phenylbis(pentafluorophenyl)borane and the like, and tris(pentafluorophenyl)borane is most preferable.

In the boron compound (D2) represented by the general formula, $G^+(BQ^1Q^2Q^3Q^4)^-$, $G^+$ is an inorganic or organic cation, B is a tri-valent boron atom, and $Q^1 \sim Q^4$ are the same as $Q^1 \sim Q^3$ in the above-mentioned (D1).

Specific examples of $G^+$ being an inorganic cation in the compound (D2) represented by the general formula, $G^+(BQ^1Q^2Q^3Q^4)^-$, include a ferrocenium cation, an alkyl-substituted ferrocenium cation, a silver cation and the like, and $G^+$ being an organic cation includes a triphenylcarbenium cation and the like. As $G^+$, a carbenium cation is preferable, and in particular, a triphenylcarbenium cation is preferable.

$(BQ^1Q^2Q^3Q^4)^-$ includes tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate, tetrakis[3,5-bis(trifluoromethyl)phenyl]borate and the like.

Specific combinations thereof include ferrocenium tetrakis(pentafluorophenyl)borate, 1,1'-dimethylferrocenium tetrakis(pentafluorophenyl)borate, silver tetrakis(pentafluorophenyl)borate, triphenylcarbenium tetrakis(pentafluorophenyl)borate, triphenylcarbenium tetrakis[3,5-bis(trifluoromethyl)phenyl]borate and the like, and triphenylcarbenium tetrakis(pentafluorophenyl)borate is most preferable.

Further, in the boron compound (D3) represented by the general formula, $(L—H)^+(BQ^1Q^2Q^3Q^4)^-$, L is a neutral Lewis base, $(L—H)^+$ is a Brønsted acid, B is a tri-valent boron atom, and $Q^1 \sim Q^4$ are the same as $Q^1 \sim Q^3$ in the above-mentioned (D1).

Specific example of $(L—H)^+$ being a Brønsted acid in the compound represented by the general formula, $(L—H)^+(BQ^1Q^2Q^3Q^4)^-$, includes a trialkyl-substituted ammonium, a N,N-dialkylanilinium, a dialkylammonium, a triarylphosphonium and the like, and $(BQ^1Q^2Q^3Q^4)^-$ includes the same one as fore-mentioned.

Specific examples of these combinations include triethylammonium tetrakis(pentafluorophenyl)borate, tripropylammonium tetrakis(pentafluorophenyl)borate, tri(n-butyl) ammonium tetrakis(pentafluorophenyl)borate, tri(n-butyl) ammonium tetrakis[3,5-bis(trifluoromethyl)phenyl]borate, N,N-dimethylanilinium tetrakis(pentafluorophenyl)borate, N,N-diethylanilinium tetrakis (pentafluorophenyl)borate, N,N-2,4,6-pentamethylanilinium tetrakis (pentafluorophenyl) borate, N,N-dimethylanilinium tetrakis [3,5-bis(trifluoromethyl)phenyl]borate, diisopropylammonium tetrakis(pentafluorophenyl)borate, dicyclohexylammonium tetrakis(pentafluorophenyl)borate, triphenylphosphonium tetrakis(pentafluorophenyl)borate, tri (methylphenyl)phosphonium tetrakis(pentafluorophenyl) borate, tri(dimethylphenyl)phosphonium tetrakis (pentafluorophenyl) borate and the like, andtri(n-butyl) ammonium tetrakis(pentafluorophenyl)borate or N,N-dimethylanilinium tetrakis (pentaf luorophenyl)borate is most preferable.

As the catalyst for olefin polymerization of the present invention, the catalyst for olefin polymerization wherein the transition metal compound represented by the above-mentioned general formula (2) or (3), and the above-mentioned (C1) and the above-mentioned (D) are used, or the catalyst for olefin polymerization wherein the transition metal compound represented by the above-mentioned general formula (2) or (3), and the above-mentioned (C2) and/or (C3) are used, is preferable. The catalyst for olefin polymerization wherein the transition metal compound represented by the above-mentioned general formula (2) or (3), and the above-mentioned (C1) and the above-mentioned (D) are used, is more preferable.

The amount of the compound (C) used can be usually selected at a wide range of 1~10000 mol as the molar amount of aluminum atom per 1 mole of a transition metal atom in the transition metal compound represented by the general formula (2) or (3) or the compound (B). A range of 1~3000 mol per 1 mole of the transition metal atom is preferable.

The amount of the compound (D) used can be usually selected at a wide range of 0.01~1000 mol as a molar amount per 1 mole of a transition metal atom in the transition metal compound represented by the general formula (2) or (3) or the compound (B). A range of 0.1~50 mol per 1 mole of the transition metal atom is preferable, and a range of 0.1~20 mol is more preferable.

As a method of charging each of the components in a polymerization vessel, it is charged in the presence of a monomer under a dry condition in an inactive gas such as, for example, nitrogen, argon or the like. The transition metal compound represented by the general formula (2) or (3), the compound (C) and the compound (D) or the bisoxazoline compound (A) represented by the general formula (1), the compound (B), the compound (C) and the compound (D) may be individually charged and may be charged after contacting in advance.

The polymerization temperature can be usually carried out over −80~300° C., preferably 0~280° C. and more preferably 20~250° C.

The polymerization pressure is not particularly restricted, and about normal pressure~about 150 kg/cm² is preferable from an industrial and economic viewpoint. The polymerization time is suitably determined according to a kind of the desired polymer and a reaction apparatus in general, and adopts a range of 5 minutes~40 hours.

As a polymerization process, either of batch type and continuous type are applicable. Further, a slurry polymerization or a solution polymerization with an inert hydrocarbon solvent such as propane, pentane, hexane, heptane, octane or the like, a liquid phase polymerization without a solvent or a gas phase polymerization is applicable.

The process for producing an olefinic polymer of the present invention is a process for producing an olefinic polymer wherein olefins are homo polymerized or olefins are copolymerized with other olefins and/or other polymerizable unsaturated compound using the catalyst for olefin polymerization previously mentioned.

As the olefins applicable to the polymerization in the present invention, olefins comprising 2 to 20 carbon atoms, in particular, ethylene, α-olefin having 3 to 20 carbon atoms, diolefins having 4 to 20 carbon atoms and the like can be used, and two or more of monomers can be used at the same time. Specific examples of the olefins include linear chain olefins such as ethylene, propylene, butene-1, pentene-1, hexene-1, heptene-1, octene-1, nonene-1, decene-1 and the like, branched olefins such as 3-methylbutene-1, 3-methylpentene-1, 4-methylpentene-1, 5-methyl-2-pentene-1 and the like, vinyl cyclohexane and the like.

However, the present invention should not be limited to the above-mentioned compounds.

Specific example of the other polymerizable unsaturated compound used in the process for producing an olefinic polymer of the present invention includes a compound selected from an acrylic acid ester compound and a methacrylic acid ester compound. Specific examples of the acrylic acid ester compound include methyl acrylate and a compound in which its methyl is changed to ethyl, n-propyl, isopropyl, n-butyl, isobutyl, tert-butyl or the like. Further, specific examples of the methacrylic acid ester compound include methyl methacrylate and a compound in which its methyl is changed to ethyl, n-propyl, isopropyl, n-butyl, isobutyl, tert-butyl or the like.

An ethylene-α-olefin copolymer is preferable as the copolymer produced by the process for producing an olefinic polymer of the present invention, and specific examples of the combination of monomers constituting a copolymer include ethylene and propylene, ethylene and butene-1, ethylene and hexene-1, ethylene and octene-1, propylene and butene-1, and the like. However, the present invention should not be limited to these combinations.

Further, a chain transfer agent such as hydrogen, a silane compound or the like can be added in order to control the molecular weight of the olefin polymer of the present invention.

EXAMPLE

The present invention is specifically illustrated according to Examples below, but the scope of the present invention is not construed to be only restricted to Examples.

Further, the measurement values of respective items in Examples were measured by methods described below.

(1) Intrinsic viscosity ($[\eta]$:dl/g):

It was measured with an Ubbelohde type viscometer at 135° C. in tetralin.

(2) Number-average molecular weight (Mn) and molecular weight distribution(Mw/Mn):

It was estimated by gel permeation chromatography (GPC) using a polystyrene as standard under conditions described below.

Apparatus: 150CV type manufactured by Millipore-Waters Company Ltd.

Column: Shodex M/S 80

Measurement temperature: 145° C.,

Solvent; o-dichlorobenzene

Concentration of sample: 5 mg/8 ml (3) Melting point (Tm ° C.):

It was measured with DSC-VII manufactured by Perkin-Elmer Company Ltd. under the condition below.

Temperature raising: 40° C.~150° C.(10° C./min.), retaining for 5 minutes.

Cooling: 150° C.~40° C.(5° C./min.), retaining for 10 minutes.

Measurement: 40° C.~160° C.(5° C./min.)

(4) $^1$H NMR spectrum:

It was recorded on a JEOL JNM-EX270 spectrometer. A deuterated solvent described in Example was used and measurement was carried out at room temperature.

(5) Mass analysis of complex:

It was carried out using a JEOL JMS-700 type mass analyser.

Respective compounds (C) and (D) used during polymerization in Example described below are as follows:

Triisobutylaluminum: Commercial product manufactured by Toso-Akzo Company Ltd. Triisobutylaluminum was diluted with toluene and used as a 1M solution.

Triethylaluminum: Commercial product manufactured by Toso-Akzo Company Ltd. Triethylaluminum was diluted with toluene and used as a 1M solution.

PMAO: PMAO-S manufactured by Toso-Akzo Company Ltd.

3M toluene solution of (poly)methylaluminoxane was used.

MMAO: Manufactured by Toso-Akzo Company Ltd.

2.25M hexane solution of (poly) methylisobutylaluminoxane was used.

Triphenylcarbenium tetrakis(pentafluorophenyl)borate: Commercial product manufactured by Toso-Akzo Company Ltd. Triphenylcarbenium tetrakis(pentafluorophenyl)borate was diluted and used as a 0.001M solution.

Reference Example 1

Under an atmosphere of nitrogen, 3.0 g (10.4 mmol) of (R)-2-amino-2-phenyl-1,1-diphenylethanol and 0.685 g (5.2 mmol) of dimethyl malonate were dissolved in 150 ml of m-xylene. The solution was stirred at 120° C. for 5 hours. Then, 147 mg (0.52 mmol) of titanium tetraisopropoxide was added to the reaction solution and the mixture was stirred at 120° C. for 48 hours.

After completion of the reaction, the m-xylene was evaporated under reduced pressure and 2.35 g (yield: 74.1%) of 2,2'-methylenebis[(4R)-4-phenyl-5,5-diphenyloxazoline] was obtained by being purified with chromatography (neutral alumina/ethyl acetate:hexane=3:2)

$^1$H NMR (CDCl$_3$, TMS) δ 3.91 (s,2H), 6.82–7.14 (m,18H), 7.33–7.43 (m,8H), 7.68 (d,4H).

Reference Example 2

2,2'-methylenebis[(4S)-4-isopropyl-5,5-diphenyloxazoline] was prepared from 2.66 g (10.4 mmol) of (S)-2-amino-3-methyl-1,1-diphenylbutanol and 0.685 g (5.2 mmol) of dimethyl malonate in 76.5% yield (pale yellow powders, 2.15 g) following the same procedure as described for Reference Example 1.

$^1$HNMR (CDCl$_3$, TMS) δ 0.64 (d,6H, J=6.9), 0.96 (d,6H, J=6.9), 1.70–1.85 (m,2H), 3.64 (s,2H), 4.63 (d,2H, J=4.9), 7.21–7.51 (m,20H).

Reference Example 3

2,2'-methylenebis[(4R)-4-phenyl-5,5-dimethyloxazoline] was prepared from 1.72 g (10.4 mmol) of (R)-2-amino-2-phenyl-1,1-dimethylethanol and 0.685 g (5.2 mmol) of dimethyl malonate in 75.4% yield (pale yellow oil, 1.42 g) following the same procedure as described for Reference Example 1.

$^1$H NMR (CDCl$_3$, TMS) δ 0.88 (s,6H), 1.60 (s,6H), 3.53 (s,2H), 4.90 (s,2H), 7.20–7.35 (m,10H).

Reference Example 4

2,2'-methylenebis[spiro{(4R)-4-phenyloxazoline-5,1'-cyclopentane}] was prepared from 1.99 g (10.4 mmol) of 1-[(R)-aminophenylmethyl]cyclopentanol and 0.685 g (5.2 mmol) of dimethyl malonate in 77.5% yield (pale yellow oil, 1.66 g) following the same procedure as described for Reference Example 1.

$^1$H NMR (CDCl$_3$, TMS) δ 1.00–1.83 (m,16H), 3.55 (s,2H), 5.01 (s,2H), 7.20–7.34 (m,10H).

Example 1

Under an atmosphere of nitrogen, 567 mg (1.40 mmol) of 2,2'-methylenebis[(4R)-4-phenyl-5,5-dimethyloxazoline]

and 400 mg (1.30 mmol) of dimethoxyethanenickel bromide were mixed with 25 ml of dichloromethane and the mixture was stirred at room temperature for 18 hours. The solvent was evaporated under reduced pressure, and the product was washed 4 times with hexane (20 ml)and dried under reduced pressure. 700 mg (yield: 93%) of 2,2'-methylenebis[(4R)-4-phenyl-5,5-dimethyloxazolinyl]nickel bromide was obtained as pale pink powder.

Example 2

Under an atmosphere of nitrogen, 323 mg (529 mmol) of 2,2'-methylenebis[(4R)-4-phenyl-5,5-diphenyloxazoline] and 163 mg (529 mmol) of dimethoxyethanenickel bromide were mixed with 25 ml of dichloromethane and the mixture was stirred at room temperature for 18 hours. The solvent was evaporated under reduced pressure, and the product was washed 4 times with (toluene:hexane=1:2, 20 ml)and dried under reduced pressure. 180 mg (yield: 41%) of 2,2'-methylenebis[(4R)-4-phenyl-5,5-diphenyloxazolinyl]nickel bromide was obtained as pale pink powder.

Example 3

Under an atmosphere of nitrogen, 250 mg (0.69 mmol) of 2,2'-methylenebis[(4R)-4-phenyl-5,5-diphenyloxazoline] prepared in Reference Example 1 and 190 mg (0.69 mmol) of bis(1,5-cyclooctadiene)nickel(0) were mixed with 23 ml of toluene in a 50 ml egg-plant type flask equipped with a stirrer and the mixture was stirred at room temperature for 18 hours. The precipitate was filtreted off using a glass filter covered with a celite and then a transition metal compound solution was obtained.

A 200 ml of purified m-xylene was placed in a 400 ml stirring type autoclave made of stainless steel under argon. 11 ml (2.5 mmol) of MMAO and 1.7 ml(50 $\mu$mol) of the transition metal compound solution previously prepared were added. Wherein a molar ratio of [Al]/[Ni] was 500. Ethylene gas at 35 kgf/cm$^2$ was fed and polymerization was carried out at room temperature for 60 minutes. Ethylene gas pressure was constantly kept during the polymerization. Then, the polymerization was quenched by injection of 15 ml of ethanol. Unreacted ethylene gas was purged, and the content of the autoclave was poured into 400 ml of ethanol in which 50 ml of 2N hydrochloric acid was added, and the polymer was precipitated. The polymer was filtrated off and dried at 60° C. for about 4 hours. As a result, 2.33 g of polyethylene was obtained. Mn=9390; Mw/Mn=52.4.

Example 4

Under an atmosphere of nitrogen, 26 mg (0.45 $\mu$mol) of 2,2'-methylenebis[(4R)-4-phenyl-5,5-dimethyloxazolinyl] nickel bromide prepared in Example 1 was dissolved in 47 ml of purified toluene in a 100 ml Schlenk tube equipped with a stirrer. The solution was cooled to 0° C., 5 ml (1.5 mmol) of PMAO was added dropwise, and the mixture was stirred for 10 minutes. Wherein a molar ratio of [Al]/[Ni] was 333.

A 150 ml of purified toluene was placed in a 400 ml stirring type autoclave made of stainless steel under argon, and the inside of the autoclave was controlled at 30° C. 10 ml (3 mmol) of PMAO and 47 ml(45 $\mu$mol) of the transition metal compound solution previously prepared were added. Wherein a molar ratio of [Al]/[Ni] in the whole system was 1000. After stirring for 5 minutes, ethylene gas at 35 kgf/cm$^2$ was fed and polymerization was carried out at 30° C. for 60 minutes. Ethylene gas pressure was constantly kept during the polymerization. Then, the polymerization was quenched by injection of 15 ml of water. The amount of ethylene consumed was 22.5 g (TON 17800h$^{-1}$). The autoclave was cooled to −50° C. or less using dry ice/ethanol, and unreacted ethylene gas was purged. The oligomer of the content of the autoclave was extracted in the Schlenk tube cooled with dry ice/ethanol, and a composition ratio was determined by gas chromatography. The composition of the oligomer was 90% of C4 component and 3% of C6 component. The solid polymer was poured into 400 ml of ethanol in which 50 ml of 2N hydrochloric acid was added, and the polymer was precipitated. The polymer was filtrated off and dried at 60° C. for about 4 hours. As a result, 460 mg of polyethylene was obtained. Wherein TON means a molar number of ethylene reacted per a catalyst mole per a unit time.

Example 5

Under an atmosphere of nitrogen, 7 mg (12 $\mu$mol) of 2,2'-methylenebis[(4R)-4-phenyl-5,5-dimethyloxazolinyl] nickel bromide prepared in Example 1 was dissolved in 12 ml of purified toluene in a 50 ml egg-plant type flask equipped with a stirrer.

A 200 ml of purified toluene was placed in a 400 ml stirring type autoclave made of stainless steel under argon, and the inside of the autoclave was controlled at 30° C. Thereto, 0.5 ml (0.5 mmol) of triisobutylaluminum and 1 ml(1 $\mu$mol) of the transition metal compound solution previously prepared were added. Wherein a molar ratio of [Al]/[Ni] was 500. After stirring at 30° C. for 5 minutes, 3 ml (3 $\mu$mol) of triphenylcarbenium tetrakis (pentafluorophenyl)borate was added and stirred. Wherein a molar ratio of [Ni]/[B] was 3. Ethylene gas at 35 kgf/cm$^2$ was fed and polymerization was carried out at 30° C. for 60 minutes. Ethylene gas pressure was constantly kept during the polymerization. Then, the polymerization was quenched by injection of 15 ml of ethanol . Unreacted ethylene gas was purged, and the content of the autoclave was poured into 400 ml of ethanol in which 50 ml of 2N hydrochloric acid was added, and the polymer was precipitated. The polymer was filtrated off and dried at 60° C. for about 4 hours. As a result, 8.40 g of polyethylene was obtained. [$\eta$]=1.8 dl/g; Mn=110000; Mw/Mn=1.7.

Example 6

The same apparatus and the same procedure as in Example 5 were carried out except that the amount of triisobutylaluminum was changed to 1mmol in Example 5 (wherein a molar ratio of [Al ]/[Ni] was 1000). As a result, 1.5 g of polyethylene was obtained. [$\eta$]=1.56 dl/g; Mn=110000; Mw/Mn=1.7.

Example 7

The same apparatus and the same procedure as in Example 5 were carried out except that triisobutylaluminum was changed to 0.5 ml (0.5mmol) of triethylaluminum in Example 5. As a result, 0.35 g of polyethylene was obtained. Mn=129000; Mw/Mn=4.6.

Example 8

Polymerization was conducted with using the same apparatus and the same procedure as in Example 5 except that 2,2'-methylenebis[(4R)-4-phenyl-5,5-dimethyloxazolinyl] nickel dibromide was changed to 2,2'-methylenebis[(4R)-4-phenyl-5,5-diphenyloxazolinyl]nickel dibromide synthesized in Example 2 and the amount of ethylene gas feed was 10 kgf/cm² As a result, 7.50 g of polyethylene was obtained. Intrinsic viscosity ([η])of the polyethylene obtained was 1.50 dl/g, number average molecular weight (Mn) was 101000, and molecular weight distribution (Mw/Mn) was 1.9.

Example 9

Under an atmosphere of nitrogen, 7 mg (12 μmol) of 2,2'-methylenebis[(4R)-4-phenyl-5,5-dimethyloxazolinyl] nickel dibromide synthesized in Example 1 was dissolved in 12 ml of purified toluene in a 50 ml egg-plant type flask equipped with a stirrer.

The atmosphere of a 400 ml stirring type autoclave made of stainless steel was replaced with argon, 200 ml of purified toluene was charged, and the inside of the autoclave was controlled at 30° C. Thereto, 0.5 ml (0.5 mmol) of triisobutylaluminum and 1 ml (1 μmol) of a solution of the transition metal compound previously prepared were added. The molar ratio of [Al]/[Ni] was 500. After the mixture was stirred at 30° C. for 5 minutes, 3 ml (3 μmol) of triphenylcarbenium tetrakis(pentafluorophenyl)borate was added and the mixture was stirred. The molar ratio of [Ni]/[B] was 3. Thereto, 30 ml of hexene-1 was added, ethylene gas at 20 kgf/cm² was fed and polymerization was carried out at 30° C. for 60 minutes. Ethylene gas was continuously fed in order to keep a pressure in the system constant in the meantime. Then, the polymerization was stopped by charging 15 ml of ethanol under pressure. Unreacted ethylene gas was purged, and the content of the autoclave was charged in 400 ml of ethanol in which 50 ml of 2N hydrochloric acid was added, and a polymer deposited was separated by filtration and dried at 60° C. for about 4 hours. As a result, 4.00 g of the polymer was obtained. Intrinsic viscosity ([η]) of the polymer obtained was 1.72 dl/g, number average molecular weight (Mn) was 102000, molecular weight distribution (Mw/Mn) was 1.7, and melting point (Tm) was 118° C.

Example 10

Polymerization was conducted with using the same apparatus and the same procedure as in Example 9 except that 2,2'-methylenebis[(4R)-4-phenyl-5,5-dimethyloxazolinyl] nickel dibromide was changed to 2,2'-methylenebis[(4R)-4-phenyl-5,5-diphenyloxazolinyl]nickel dibromide synthesized in Example 2, the amount of hexene-1 was changed to 15 ml, and the amount of ethylene gas fed was changed to 5 kgf/cm². As a result, 6.40 g of a polymer was obtained. Intrinsic viscosity ([η]) of the polymer obtained was 1.08 dl/g, number average molecular weight (Mn) was 82000, molecular weight distribution (Mw/Mn) was 1.8, and melting point (Tm) was 103° C.

Example 11

Polymerization was conducted with using the same apparatus and the same procedure as in Example 5 except that hexene-1 was changed to 20 g of butene-1 in Example 10. As a result, 4.0 g of a polymer was obtained. Intrinsic viscosity ([η]) of the polymer obtained was 0.99 dl/g, number average molecular weight (Mn) was 89000, molecular weight distribution (Mw/Mn) was 1.7, and melting point (Tm) was 64° C.

According to the present invention, a new transition metal compound being able to be easily synthesized, a catalyst component for olefin polymerization comprising said transition metal compound, a catalyst for olefin polymerization exhibiting a high polymerization activity in polymerization of the olefin using said transition metal compound, and a process for efficiently producing an olefinic homopolymer and copolymer using said catalyst for olefin polymerization, are provided.

What is claimed is:

1. A catalyst for olefin polymerization wherein (A), (B), and (C) and/or (D) described below are combined:
    (A); a bisoxazoline compound represented by the general formula (1) described below,

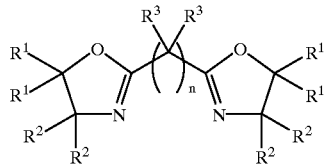

(1)

wherein; each of $R^1$, $R^2$ and $R^3$ independently represents a hydrogen atom, a halogen atom, an alkyl group, an aryl group, an aralkyl group, an alkoxy group, an aryloxy group, an aralkyloxy group, or a cyano group, all of $R^1$s, all of $R^2$s and all of $R^3$s are the same or different respectively, and they are optionally bonded to each other to form a ring; provided that all of $R^1$s are not hydrogen atoms at the same time; the symbol "n" represents an integer satisfying the equation; $0 \leq n \leq 5$;
    (B); a compound of nickel, palladium, cobalt, rhodium or ruthenium,
    (C) one or more aluminum compounds selected from the group consisting of (C1) to (C3) described below:
        (C1); an organoaluminum compound represented by the general formula, $E^1{}_a AlZ_{3-a}$,
        (C2); a cyclic aluminoxane having a structure represented by the general formula, $\{-Al(E^2)-O-\}_b$, and
        (C3); a linear aluminoxane having a structure represented by the general formula, $E^3\{-Al(E^3)-O-\}_c AlE^3{}_2$,
            wherein each of $E^1$, $E^2$ and $E^3$ is a hydrocarbon group, and all of $E^1$s, all of $E^2$s and all of $E^3$s are the same or different, Z represents a hydrogen atom or a halogen atom and all of Zs are the same or different, the symbol "a" represents a numeral satisfying the equation $0<a \leq 3$, b represents a numeral of 2 or more, and c represents an integer of 1 or more;
    (D) a boron compound of any one of (D1)–(D3) described below:
        (D1); a boron compound represented by the general formula, $BQ^1Q^2Q^3$,
        (D2); a boron compound represented by the general formula, $G^+(BQ^1Q^2Q^3Q^4)^-$,
        (D3); aboron compound represented by the general formula, $(L-H)^+(BQ^1Q^2Q^3Q^4)^-$,
            wherein B is a tri-valent boron atom,
            $Q^1$, $Q^2$, $Q^3$ and $Q^4$ each independently is a halogen atom, an alkyl group, a halogenated alkyl group, a substituted silyl group, an alkoxy group or a di-substituted amino group and they are the same or different, $G^+$ is an inorganic or organic cation, and L is a neutral Lewis base and $(L-H)^+$ is a Brønsted acid.

2. The catalyst for olefin polymerization according to claim 1 wherein (B) is a compound of nickel or palladium.

3. The catalyst for olefin polymerization according to claim 2, wherein (B) is a compound of nickel.

4. A catalyst for olefin polymerization wherein a transition metal compound represented by the following formula (2) or (3):

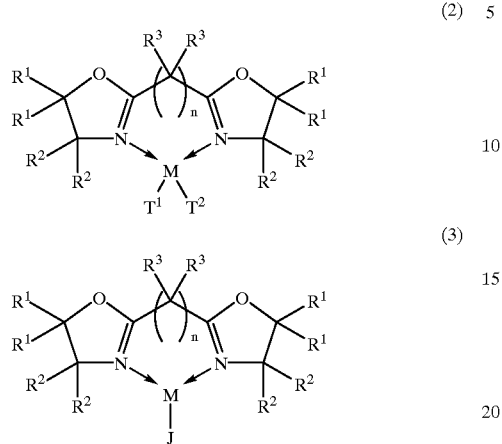

(2)

(3)

wherein M represents a nickel atom, a palladium atom, a cobalt atom, a rhodium atom or a ruthenium atom; J represents a compound coordinated to M; each of $R^1$, $R^2$ and $R^3$ independently represents a hydrogen atom, a halogen atom, an alkyl group, an aryl group, an aralkyl group, an alkoxy group, an aryloxy group, an aralkyloxy group or a cyano group; all of $R^1$s, all of $R^2$s and all of $R^3$s are the same or different respectively; they are optionally bonded to each other to form a ring; all of $R^1$s are not hydrogen atoms at the same time; the symbol "n" represents an integer satisfying the equation, $0 \leq n \leq 5$; each of $T^1$ and $T^2$ independently represents a hydrogen atom, a halogen atom, an alkyl group, an aryl group, an aralkyl group, an alkoxy group, an aryloxy group, an aralkyloxy group, a sulfonyloxy group or a substituted silyl group; $T^1$ and $T^2$ are optionally bonded to each other to form a ring, and (C) and/or (D) described below are combined;

(C) is one or more aluminum compounds selected from group consisting of (C1)–(C3) described below:

(C1); an organoaluminum compound represented by the general formula, $E^1{}_a AlZ_{3-a}$, (C2); a cyclic aluminoxane having a structure represented by the general formula, $\{-Al(E^2)-O-\}_b$, and (C3); a linear aluminoxane having a structure represented by the general formula, $E^3\{-Al(E^3)-O-\}_c AlE^3{}_2$, wherein each of $E^1$, $E^2$ and $E^3$ is a hydrocarbon group, and all of $E^1$s, all of $E^2$s and all of $E^3$s are the same or different, Z represents a hydrogen atom or a halogen atom and all of Zs are the same or different, the symbol "a" represents a numeral satisfying the equation; $0<a\leq 3$, b represents a numeral of 2 or more, and c represents an integer of 1 or more, (D) a boron compound of any one of (D1)–(D3) described below:

(D1); a boron compound represented by the general formula, $BQ^1Q^2Q^3$, (D2); a boron compound represented by the general formula, $G^+(BQ^1Q^2Q^3Q^4)^-$, (D3); aboron compound represented by the general formula, $(L-H)^+(BQ^1Q^2Q^3Q^4)^-$, wherein B is a tri-valent state, $Q^1$, $Q^2$, $Q^3$ and $Q^4$ each independently is a halogen atom, an alkyl group, a halogenated alkyl group, a substituted silyl group, an alkoxy group or a di-substituted amino group and they are the same or different, $G^+$ is an inorganic or organic cation, and L is a neutral Lewis base and $(L-H)^+$ is a Brønsted acid.

5. The catalyst for olefin polymerization according to claim 4, wherein M is a nickel atom or palladium atom.

6. The catalyst for olefin polymerization according to claim 5, wherein M is a nickel atom.

* * * * *